United States Patent [19]

Schaefer et al.

[11] Patent Number: 5,288,147
[45] Date of Patent: Feb. 22, 1994

[54] THERMOPILE DIFFERENTIAL THERMAL ANALYSIS SENSOR

[75] Inventors: John W. Schaefer, Wilmington, Del.; Robert L. Danley, Collingswood, N.J.

[73] Assignee: TA Instruments, Inc., New Castle, Del.

[21] Appl. No.: 973,416

[22] Filed: Nov. 9, 1992

[51] Int. Cl.⁵ .......................................... G01N 25/00
[52] U.S. Cl. .................................... 374/10; 136/225; 374/31; 374/179
[58] Field of Search .................. 374/10, 179, 112, 11, 374/29, 30, 31; 136/236.1, 225

[56] References Cited

U.S. PATENT DOCUMENTS

| | | |
|---|---|---|
| 3,099,575 | 7/1963 | Hill . |
| 3,263,484 | 8/1966 | Watson et al. . |
| 3,298,220 | 1/1967 | Stone et al. ........................... 374/13 |
| 3,554,002 | 1/1971 | Harden et al. . |
| 4,095,453 | 6/1978 | Woo . |
| 4,110,124 | 8/1978 | Robertson et al. . |
| 4,350,446 | 9/1982 | Johnson . |
| 4,451,690 | 5/1984 | Ishida . |
| 4,553,852 | 11/1985 | Derderian et al. ............... 374/10 X |
| 4,848,921 | 7/1989 | Kunze . |
| 5,033,866 | 7/1991 | Kehl et al. . |

Primary Examiner—Daniel M. Yasich
Attorney, Agent, or Firm—Kirkland & Ellis

[57] ABSTRACT

A differential thermal analysis sensor consisting of two low-impedance differential thermopiles. Each thermopile consists of a series of thermocouples joined in series, with the measuring junctions of the thermocouples arranged around a uniform temperature measuring region, and the thermoelectric reference junctions of the thermocouples arranged around a uniform temperature thermoelectric reference region. The differential thermal analysis sensor can be used for single-sample heat flux differential thermal analysis measurements, dual-sample heat flux differential thermal analysis measurements, or power compensation differential thermal analysis measurements.

43 Claims, 9 Drawing Sheets

THERMOPILE DIFFERENTIAL THERMAL ANALYSIS SENSOR

BACKGROUND

1. Field of the Invention

This invention relates to sensors used in differential thermal analyzers such as differential scanning calorimeters.

2. Background of the Invention

Differential thermal analyzers measure the difference in temperature between a sample material and a reference material, as the sample and reference materials are subjected to dynamic controlled changes of temperature. Measurement of the dynamic temperature difference as a function of temperature provides qualitative information concerning physical transformations which occur in the sample material. Differential scanning calorimeters are differential thermal analyzers which provide quantitative information about physical transformations occurring in the sample by measuring the flow of heat to or from the sample.

Differential scanning calorimeters fall into two broad classes of instruments: heat flux instruments and power-compensated instruments. Heat flux differential scanning calorimeters measure the dynamic temperature difference between a sample material and a reference material. Because the dynamic temperature difference is proportional to the heat flow to (or from) the sample, the heat flow to (or from) the sample is obtained from the dynamic temperature difference. Power compensated differential scanning calorimeters control the flow of heat to the sample material and reference material separately. The flow of heat is controlled so as to maintain the temperature of the sample material at the temperature of the reference material during physical transformations in the sample material. The heat flow to (or from) the sample material is calculated from the difference between power supplied to the sample material and the power supplied to the reference material.

Heat flux calorimeters comprise means for supporting the sample and reference materials, a temperature sensor to determine the temperature of the sample material, a differential temperature sensor to measure the difference between the temperature of the sample material and the temperature of the reference material, and a controlled-temperature enclosure. U.S. Pat. No. 4,095,453 to Woo describes a typical means for supporting a sample or reference material in a differential scanning calorimeter. The most typical type of support means is a circular disk but this is by no means the only configuration used. For example, some high sensitivity differential scanning calorimeters have receptacles mounted on short columns attached to the disk to hold the sample pans. The columns increase the heat flow resistances between the disk and the sample pans, thereby increasing the temperature difference between sample and reference and hence the sensitivity of the differential scanning calorimeter. However, this decreases the resolution in proportion to the increase in sensitivity. The enclosure may be supplied with a cooling device to more accurately control its temperature or for below-room temperature measurements.

Most instruments use thermoelectric effect differential temperature sensors, i.e., thermocouples, wherein a difference in the measurement temperature and a reference temperature generates an electromotive force proportional to the temperature difference between the measuring and thermoelectric reference temperatures.

There are two types of commonly-used differential temperature sensors based upon the thermoelectric effect. The differential thermocouple uses a single differential temperature-sensing element. The differential thermopile uses multiple, in-series differential thermocouples. U.S. Pat. No. 3,554,002 to J.C. Harden et al. describes a differential thermal analysis cell using a differential thermocouple. U.S. Pat. No. 5,033,866 to Kehl et al. describes a thermal analysis sensor using a differential thermopile.

The resolution and calorimetric sensitivity of an instrument are two of the important performance criteria for differential scanning calorimeters. These criteria serve to define the applications for which the instrument is best suited. Resolution is the instrument's ability to separate thermal events which occur at temperatures which are close to each other. It is determined by the dynamic thermal response of the instrument. Calorimetric sensitivity is the measure of the signal generated by an instrument in response to a thermal event having a certain heat flow. Dynamic thermal behavior is characteristic of the geometry of a particular instrument, and of the materials used in its construction.

The sensitivity of heat flux instruments is dependent upon the output of the differential temperature sensor, which is in turn dependent upon, in part, the temperature difference developed between the sample material and the reference material. This temperature difference is also dependent upon the instrument geometry and construction materials. However, there is an inverse relationship between instrument designs that improve resolution and instrument designs that improve sensitivity. For an instrument using a given type and configuration of differential temperature sensor, increasing sensitivity results in decreased resolution while increased resolution results in decreased sensitivity.

Thermopile instruments are capable of greater sensitivity, because the output signal of the sensor is increased in proportion to the number of thermocouples in the thermopile. However, geometric considerations eventually limit the performance of the instrument, because the number of differential thermocouples which fit into an instrument of a given size is limited.

Another very important measure of performance of differential scanning calorimeters is their signal-to-noise ratio. This ratio is a measure of the smallest heat flow detectable by the instrument. Noise in differential thermal analyzers is predominantly electromagnetic and amplifier noise. Sensors with low electrical impedance pick up less noise than sensors with high electrical impedance. Differential thermopile sensors have inherently high electrical impedance. Thermopile sensors are therefore highly susceptible to electromagnetic noise and thus have a decreased signal-to-noise ratio.

The heat flow is measured as a function of the sample temperature. The preferred method for measuring the temperature of the sample is to directly measure the sample temperature using a sample temperature sensor. An alternate but less desirable approach is to use the temperature of the enclosure as a measure of the sample temperature. U.S. Pat. No. 4,095,453 discloses an instrument that directly measures sample temperature. U.S. Pat. No. 5,033,866 discloses an instrument wherein the sample temperature is inferred from the enclosure temperature.

U.S. Pat. No. 4,350,446 describes a heat flux differential scanning calorimeter which can measure multiple samples simultaneously. Although this instrument improves productivity, in practice its calorimetric accuracy and precision is not equal to that of single-sample instruments. The user of such instruments must choose between accuracy and precision, and productivity, or must use separate single-sample and multiple sample instruments.

U.S. Pat. No. 3,263,484 describes power compensation differential scanning calorimetry. Power compensation calorimeters measure the difference in power supplied to the sample material and the reference material, and determine the heat flow from this measurement. Heat flux instruments calculate the heat flow from a differential temperature measurement. However, power compensation instruments are more complex than heat flux instruments.

Moreover, current power compensation instruments do not directly measure sample temperature.

Furthermore, there are no current instruments that can be used either as power compensation instruments or as heat flux instruments. A user who wants to practice both techniques would have to purchase instruments of each type.

In traditional differential scanning calorimetry, the sample material and the reference material are simultaneously subjected to the regulated temperature environment. However, this is not essential to the operation of the calorimeter. Differential scanning calorimetry may be performed sequentially, by subjecting the sample material and the reference material to consecutive measurements, storing the results, and subsequently calculating the heat flow to (and from) the sample. U.S. Pat. No. 4,848,921 describes this technique in power compensation calorimeters. In principle, heat flux calorimeters could also measure the heat flow to (and from) the sample material and the reference material sequentially.

Differential thermocouples and thermopiles, in addition to being used to measure temperature difference, may transfer energy between the measuring and reference points by employing the Peltier effect. The Peltier effect describes the behavior of a thermocouple circuit when direct electric current is applied to it. When an electric current is applied to the differential thermocouple, one of the two thermocouple junctions is heated and the other is cooled. This difference in temperature corresponds to a flow of heat from the colder to the hotter junction. Thus the Peltier effect refers to the use of a thermocouple as a heat pump. The magnitude of the Peltier effect is strongly dependent on the electrical impedance of the thermocouple: for a given type of thermocouple, thermocouples with low electrical impedance have greater heat pumping capacity than those with higher impedance. The current supplied to the differential thermocouple or thermopile is a measure of the heat pumped by the Peltier effect, as described in U.S. Pat. No. 4,451,690.

SUMMARY OF THE INVENTION

The present invention is a dual differential thermopile sensor for use in differential thermal analysis and differential scanning calorimetry. The differential thermal analysis sensor can be used for single-sample heat flux, dual-sample heat flux, single-sample power compensation, or dual-sample power compensation measurements.

The differential thermal analysis sensor of the present invention comprises a flat substrate which supports two low-impedance differential thermopiles. The thermopiles are arranged such that the measuring junctions of the two thermopiles measure temperature or temperature differentials at separate positions. The thermoelectric reference junctions are distributed about the periphery of the substrate such that each junction is coincident with the corresponding junction of the other thermopile. An absolute temperature thermocouple is also mounted on the substrate at each of the two measuring positions. This sensor, installed in a controlled-temperature thermal analysis enclosure, constitutes with the enclosure a differential thermal analyzer or a differential scanning calorimeter.

In a first preferred method of using the differential thermal analysis sensor of the present invention, a sample material is placed on one measuring position and a reference material is placed on the other measuring position. The temperature of the enclosure is controlled at the desired heating rate as the output from the two thermopiles is combined such that the difference between the temperature of the sample material and the reference material is obtained. This difference in temperature is directly proportional to the flow of heat to or from the sample. This method can be used to practice high precision single-sample heat flux differential scanning calorimetry.

In a second preferred method of using the differential thermal analysis sensor of the present invention, two reference materials are placed on each of the measuring positions. The difference in temperature between each of the reference materials and the thermoelectric reference temperature of the thermopiles is then measured as the temperature of the enclosure is controlled at the desired heating rate. The signal from each of the thermopiles is recorded and stored in a computer memory. A sample material is then placed on each of the measuring positions and the same temperature program is executed. Again, the signal from each of the thermopiles is recorded and stored in computer memory. The signal from the reference and sample runs are combined by subtracting the reference signal from the sample signal after the sample signals and reference signals have been separated. The combined signal can thus be used to practice dual-sample heat flux differential scanning calorimetry.

In a third preferred method of using the differential analysis sensor of the present invention, a sample material is placed on one measuring position, and a reference material is placed on the other reassuring position. The temperature of the enclosure is controlled at the desired heating rate. Controlled direct electrical currents are supplied individually to the two thermopiles such that the temperature difference between sample and reference which would otherwise occur is suppressed by the Peltier effect. The difference in the electrical current supplied to the sample thermopile and to the reference thermopile is measured and recorded. The difference in the direct electrical currents is proportional to the heat flow to (or from) the sample. Thus this method can be used to practice power compensated differential scanning calorimetry.

Thus, according to the present invention, any or all of the four basic differential analysis methods (single-sample heat flux, dual-sample heat flux, single-sample power compensated and dual-sample power compensated calorimetry) may be practiced in a single instrument.

Theory—Single-sample Reat Plux Differential Scanning calorimetry

For N differential thermocouples in each of the two thermopiles, the electromotive force generated by the thermopile is proportional to the sum of the individual temperature differences. For the sample thermopile, the total temperature difference is given by:

$$\Delta Ts = \sum_{i=1}^{N} (Ts_i - Ttr_i),$$

where $Ts_i$ is the $i^{th}$ sample material temperature and $Ttr_i$ is the $i^{th}$ thermoelectric reference temperature. Similarly the total temperature difference for the reference thermopile is given by:

$$\Delta Tr = \sum_{i=1}^{N} (Tr_i - Ttr_i),$$

Where $Tr_i$ is the $i^{th}$ reference material temperature and $Ttr_i$ is the $i^{th}$ thermoelectric reference temperature. Subtracting the reference signal from the sample signal (which is the equivalent of electrically connecting the two thermopiles in series with opposite polarity) gives:

$$\Delta Ts - \Delta Tr = \sum_{i=1}^{N} (Ts_i - Ttr_i) - (Tr_i - Ttr_i) =$$

$$\sum_{i=1}^{N} (Ts_i - Tr_i) = \Delta Tsr,$$

i.e., the signal obtained is the sum of the temperature differences between corresponding points within the sample and reference temperature regions. This temperature difference is identical to that of a single thermopile differential scanning calorimeter. This simple result is due to the symmetry of the two thermopiles and the co-location of the thermoelectric reference junctions of the two thermopiles.

Theory—Dual-sample Reat Flux Differential Scanning Calorimetry

The major problem to overcome with the dual-sample DSC is thermal crosstalk. Because the two thermopiles have a common substrate, thermal events which occur at either measuring position will appear at the output of both thermopiles. The signal appearing on one thermopile from an event occurring on the measuring position of the other thermopile will be attenuated and delayed in time. This effect can be removed from the primary signal by processing the signal as discussed below.

The signal from one thermopile is given by:

$$A(t) = A'(t) + K_b B'(t - \tau_b)$$

Where A(t) is the thermopile output as a function of time t, A'(t) is the signal from the material on the thermopile, B'(t−$\tau_b$) is the signal from the material on the other thermopile including the time delay $\tau_b$, and $K_b$ is the fraction of the B' signal appearing in signal A.

Similarly for the other thermopile:

$$B(t) = B'(t) + K_a A'(t - \tau_a)$$

Because of the symmetry of the configuration of the dual thermopile, we can assume that $K_a = K_b = K$ and $\tau_a = \tau_b = \tau$. The desired signals are A' and B', the signals from the materials at each measuring position:

$$A'(t) = A(t) - KB'(t - \tau)$$

$$B'(t) = B(t) - KA'(t - \tau)$$

Letting t = t − $\tau$:

$$B'(t - \tau) = B(t - \tau) - KA'(t - 2\tau)$$

Substituting in the equation for A'(t) gives:

$$A'(t) = A(t) - KB(t - \tau) + K^2 A'(t - 2\tau)$$

After making a similar substitution for A'(t−2$\tau$) we get, $$A'(t) = A(t) - KB(t - \tau) + K^2 A(t - 2\tau) + K^2 A(t - 2\tau) - K^3 B'(t - 3\tau)$$

With continued substitution, we obtain an infinite series giving the desired signals, A'(t) and B'(t) in terms of the output from the two thermopiles:

$$A'(t) = A(t) - KB(t - \tau) + K^2 A(t - 2\tau) -$$
$$K^3 B(t - 3\tau) + \ldots + K^{(n+1)} (((1 + (-1)^{n+1})/2) A (t -$$
$$(n - 1)\tau) - ((1 + (-1)^n)/2) B(t - (n - 1)\tau))$$

$$B'(t) = B(t) - KA(t - \tau) + K^2 B(t - 2\tau) -$$
$$K^3 A(t - 3\tau) + \ldots + K^{(n+1)} (((1 + (-1)^{n+1})/2) B (t -$$
$$(n - 1)\tau) - ((1 + (-1)^n)/2) A(t - (n - 1)\tau))$$

Dual-sample differential scanning calorimetry according to this method comprises placing a reference material at each of the two measuring positions and heating the two reference materials according to a controlled dynamic heating program, using, e.g., a linear temperature ramp. The signals are then separated according to the above equations and the results are stored as a function of the temperature of the reference materials. Next, the two sample materials are heated using the same controlled dynamic heating program, and the two signals are also separated and stored. Finally, the difference between each of the separated sample signals and its respective separated reference signal is calculated. These difference signals are the temperature differences between the sample material and the reference material as a function of the temperature of the sample material for each sample. The reference run need only be made once and the results stored. Many sample runs may then be made and the separated signals combined with the stored results of the reference run.

Definitions

CALORIMETRIC SENSITIVITY is the magnitude of the electrical signal developed by the sensor in response to a given sample heat flow. Calorimetric sensitivity of a thermoelectric sensor is expressed in units of voltage/heat flow such as microvolts/milliwatt.

VERY HIGH CALORIMETRIC SENSITIVITY: >15 $\mu$V/mW, preferably >25 $\mu$V/Mw

HIGH CALORIMETRIC SENSITIVITY: 5 to 15 μV/MW

RESOLUTION, as used herein, is the ability to separate distinct thermal events. To completely separate thermal events, the temperature peak created during a thermal event must return to the transition baseline before the next event occurs. The speed of the return to baseline is a measure of the ability to separate transitions, and, hence, a measure of resolution. Because the decay of the temperature peak is exponential in time, the return to baseline is asymptotic. For exponentially decaying phenomena the time constant of the decay is widely used. The time constant is the time for the signal to decay to 1/e of the difference between the signal peak and the baseline. The time constant is thus a measure of the resolution.

MODERATE RESOLUTION: instruments with a time constant of approximately 5 seconds.

HIGH RESOLUTION: instruments with a time constant less than 2 seconds.

COMMON REFERENCE ZONE: For the dual thermopile differential thermal analysis sensor, the common reference zone is the annular region at the edge of the substrate which contains the thermoelectric reference junctions.

TEMPERATURE CONTROLLED ZONE: When the sensor is used in the power compensated mode, the regions of the sensor containing the sample and reference materials are temperature controlled zones. The thermopiles operate as Peltier heat pumps to transfer heat to and from those regions and thus the sample and reference regions of the sensor become temperature controlled zones.

HEAT SINK/SOURCE ZONE: Heat pumps must have a heat source from which heat can be drawn and a heat sink to which heat can be rejected. In power compensated DSCs the heat source and sink is the controlled temperature environment. The edge of the sensor disk is physically coupled to the controlled temperature environment so that heat can be pumped to and from the enclosure as required. Heat is pumped by the thermopiles using the Peltier effect.

LOW IMPEDANCE (OF THE THERMOPILES): <50 Ω. There are three sources of electrical noise which are affected by thermopile impedance. These are induced noise which is related to voltages induced in the sensor by amplifier input current noise; susceptibility to radiated emissions (from within and without the instrument system) for which the thermopile behaves like an antenna; and resistor noise. Noise from all three sources is reduced by reducing thermopile impedance. Given our current amplifier technology, noise induced by input current noise becomes a problem at 50 Ω, and resistor noise becomes a problem at 100 Ω. However, susceptibility to radiated noise is difficult to assess in general, because it depends to some degree on the operating environment.

OBJECTS OF THE INVENTION

It is a first object of the present invention to provide a sensor that can be used for single-sample heat flux, dual-sample heat flux and power compensated differential thermal analysis.

It is a second object of the present invention to provide a high resolution differential thermal analysis sensor and instrument.

It is a third object of the present invention to provide a high sensitivity differential thermal analysis sensor and instrument.

It is a fourth object of the present invention to provide a differential thermal analysis sensor having both good sensitivity and good resolution.

It is a fifth object of the present invention to provide a low-noise high-sensitivity differential thermopile sensor and instrument.

These and other objects of the present invention are described in greater detail in the detailed description of the invention, the appended drawings and the attached claims.

DETAILED DESCRIPTION OF PREFERRED EMBODIMENTS OF THE INVENTION

Dual Thermopile Differential Temperature Sensor

Figure 1:
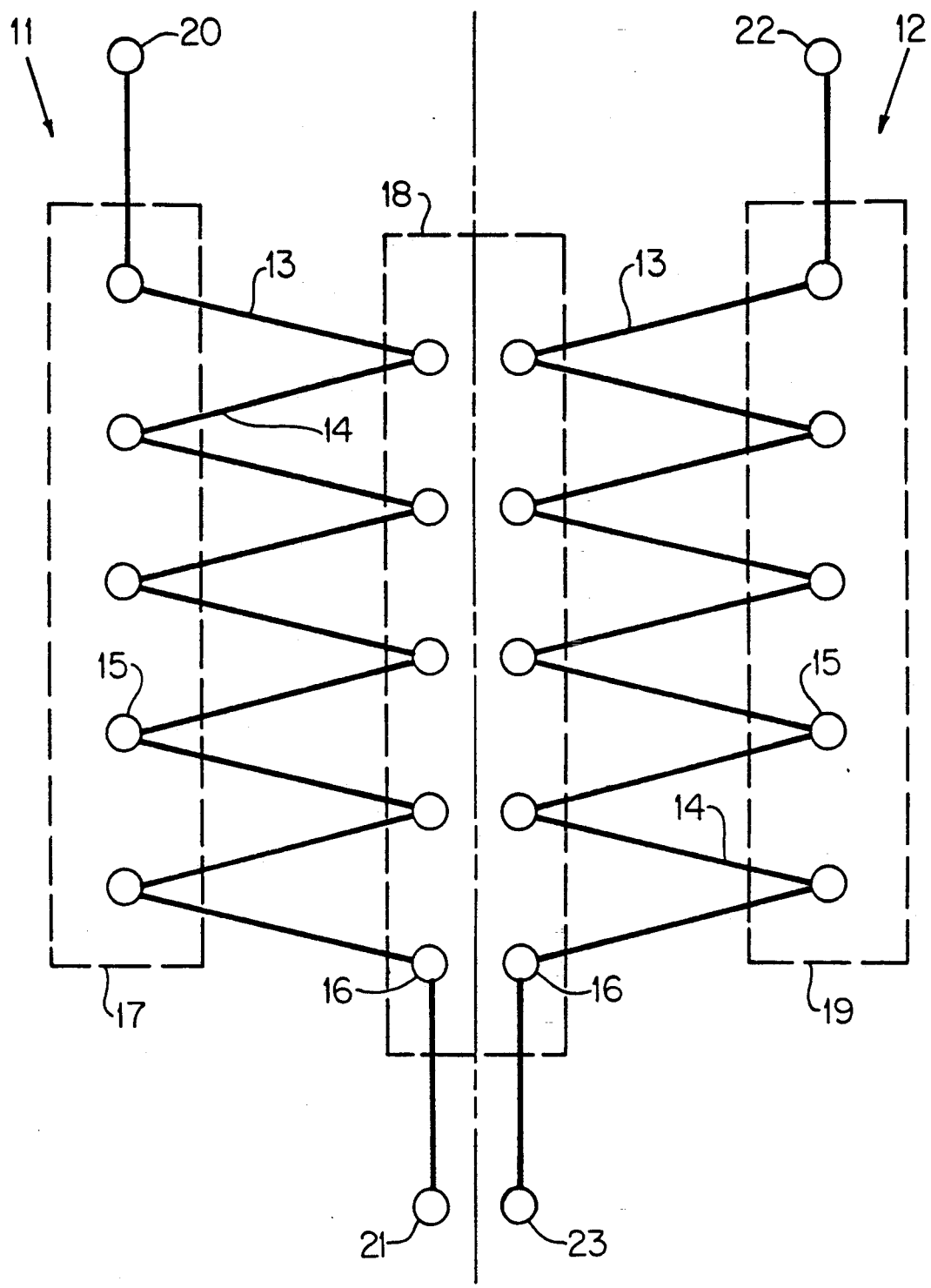
FIG. 1 is a schematic representation of the electrical circuit of the differential thermal analysis sensor of the present invention.

FIG. 1 is a schematic drawing of the electrical circuit of the dual thermopile differential temperature sensor. This sensor may be used in single-sample heat flux, dual-sample heat flux or power-compensation calorimeters. Each of the thermopiles 11 and 12 consists of conductors formed from thermoelements 13 and 14. Thermopile 11 may be used for the sample material and thermopile 12 may be used for the reference material. Thermoelement 14 is the positive thermoelement material, and thermoelement 13 is the negative thermoelement material. A thermocouple junction is formed at each point where positive thermoelement 14 and negative thermoelement 13 join. Alternating thermocouple junctions 15 (on the outside) and 16 (at the center) are measuring and thermoelectric reference junctions respectively. Each in-series pair of measuring and thermoelectric reference junctions generates an electromotive force proportional to the temperature difference between the junctions. The dual differential thermopile sensor is formed by electrically connecting the measuring and thermoelectric reference junctions in series, as shown in FIG. 1 (discussed in detail below).

The electromotice force generated by sample thermopile 11 and reference thermopile 12 is the arithmetic sum of the electromotive forces of the individual thermocouples in each thermopile, respectively. The measuring junctions of thermopile 11 are at substantially the same temperature as each other because the measuring junctions are all placed in a region of essentially uniform temperature (region 17 where the sample material is placed). Similarly, the measuring junctions of thermopile 12 are at substantially the same temperature as each other because the measuring junctions are all placed in a region of essentially uniform temperature (region 19 where the reference material is placed). The thermoelectric reference junctions are also at substantially the same temperature as each other because the thermoelectric reference junctions are all placed in a region of essentially uniform temperature (region 18). Thus the electromotive force generated by each thermopile is a measure of the temperature difference between the uniform temperature region wherein the measuring junctions are placed, and the uniform temperature region where the thermoelectric reference junctions are placed.

Thus in FIG. 1 the measuring junctions 15 of thermopile 11 are located in uniform temperature region 17, the measuring junctions 15 of thermopile 12 are located in uniform temperature region 19, and the reference junctions 16 of both thermopiles 11 and 12 are located in uniform temperature region 18. The electromotive force which is developed across terminals 20 and 21 of thermopile 11 is thus proportional to the difference in temperature between sample material region 17 and thermoelectric reference region 18, and to the number of pairs of measuring junctions 15 and reference junctions 16 which are connected in series. Similarly, the electromotive force which is developed across the terminals 22 and 23 of thermopile 12 is proportional to the difference in temperature between reference material region 19 and thermoelectric reference region 18 and to the number of pairs of measuring junctions 15 and reference junctions 16 which are connected in series. The electrical signal developed by thermopiles 11 and 12 may be increased by increasing the number of pairs of measuring and thermoelectric reference thermocouple junctions.

In the preferred embodiment of the differential thermal analysis sensor, the number of pairs of measuring junctions 15 and thermoelectric reference junctions 16 are preferably the same in thermopiles 11 and 12.

Figure 2:
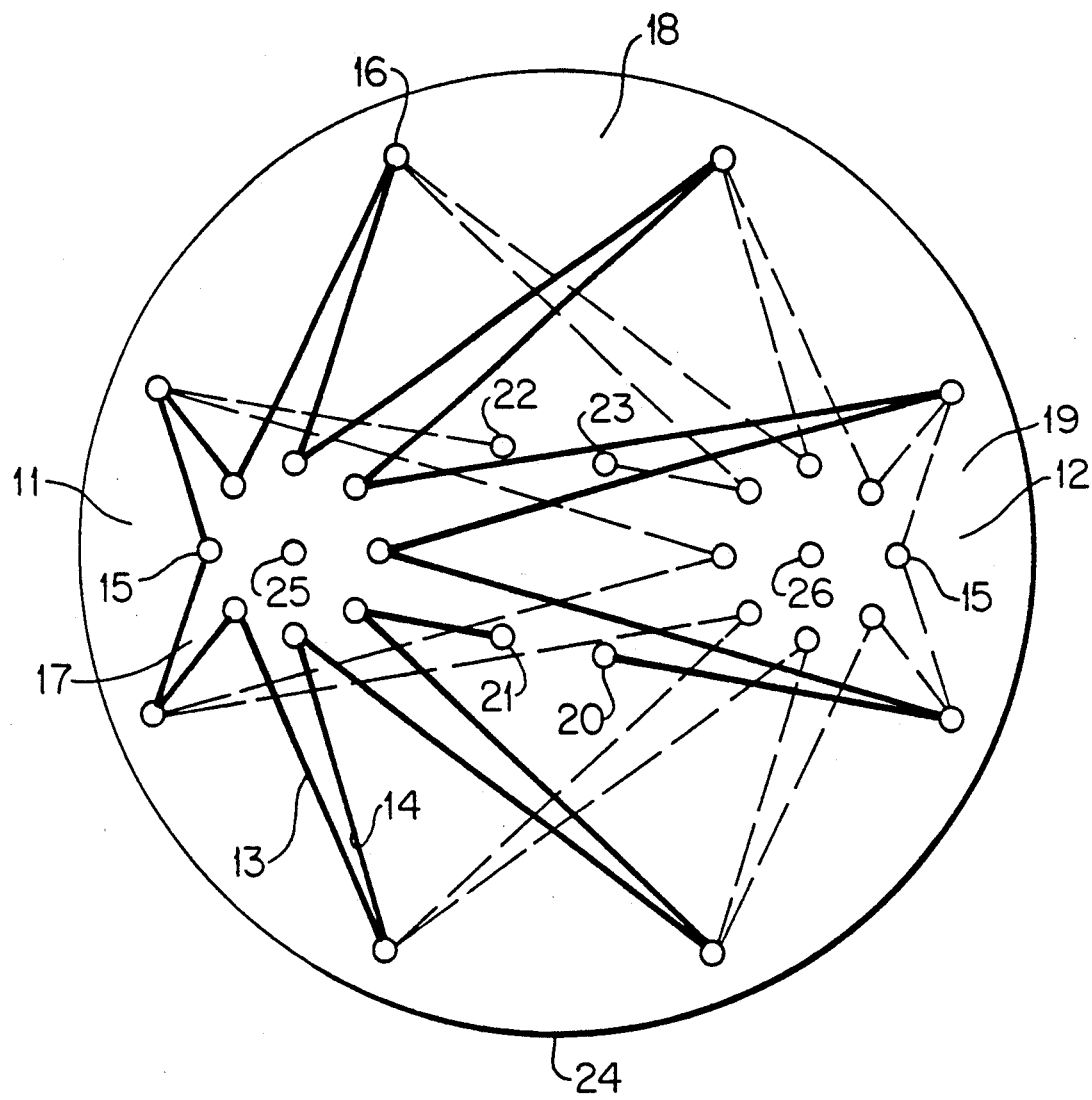
FIG. 2 is a schematic representation of the physical layout of the differential thermal analysis sensor of the present invention.

FIG. 2 illustrates the configurations of thermopiles 11 and 12, and their respective reassuring and thermoelectric reference thermocouple junctions. Thermopiles 11 and 12 are applied to substrate 24. In a preferred embodiment, substrate 24 is circular. Measuring junctions 15 are arranged in two groups on substrate 24, thus forming measuring region 17 for the sample material and measuring region 19 for the reference material. In a preferred embodiment, the sample material measuring junctions 15 are arranged in a small circular pattern to form sample material measuring region 17, and the reference material thermocouple junctions are arranged in a small circular pattern to form reference material measuring region 19. As shown in FIG. 2, measuring regions 17 and 19 are equal in size and are preferably placed symmetrically on either side of the center of substrate 24.

The thermoelectric reference junctions 16 of thermopiles 11 and 12 are arranged around the circumference of substrate 24, thus forming reference region 18. The measuring junctions 15, in regions 17 and 19, and the thermoelectric reference junctions 16 in region 18, are equally spaced about their respective circles. Furthermore, the thermoelectric reference junctions 16 of thermopile 12 are located as close as is practicable to the thermoelectric reference junctions 16 of thermopile 11. Thus thermopiles 11 and 12 are symmetrically positioned on the substrate 24, with their respective thermoelectric reference junctions occupying nearly coincident positions within the thermoelectric reference temperature region 18. The terminals 20 and 21 of thermopile 11 may be located at any position within the thermopile, interrupting either the positive or negative thermoelement. Terminals 20 and 21 are shown interrupting a positive thermoelement in FIG. 2. Similarly terminals 22 and 23 of thermopile 12 are formed by interrupting a positive or negative thermoelement. Terminals 22 and 23 are shown interrupting a positive thermoelement in FIG. 2. Preferably, terminals 20/21 interrupt a positive thermoelement, in which case terminals 22/23 must interrupt a positive thermoelement. If terminals 20/21 interrupt a negative thermoelement, then terminal 22/23 must interrupt a negative thermoelement. At the center of sample material measuring region 17 thermocouple 25 is mounted to the substrate 24 to provide an absolute measurement of the sample temperature. Similarly, at the center of reference material measuring region 19, thermocouple 26 is mounted to substrate 24 to provide a direct measurement of the reference material temperature. The thermocouples are formed by junction of two thermoelement wires (not shown) which are bonded to the pads shown in FIG. 2.

Thermoelements 13 and 14 may be applied to substrate 24 using techniques commonly employed in fabrication of electronic devices and circuits. The processes used in the manufacture of hybrid electronic circuits are particularly applicable. These processes include "thin film" techniques such as physical vapor deposition processes, and "thick film" techniques such as silk screen printing.

The thermoelement materials forming the thermocouples should be selected for their thermoelectric generating capability and their physical stability over a wide range of temperatures. Noble metals and their alloys, such as gold/gold-palladium or platinum/-platinum-rhodium, are particularly well suited for use as thermoelements in the present invention. Such noble metals are exceptionally stable and capable of generating sufficient electromotive voltages. The noble metals, and alloys of noble metals, are widely used in the above-mentioned electronic device fabrication processes.

Figure 3A:
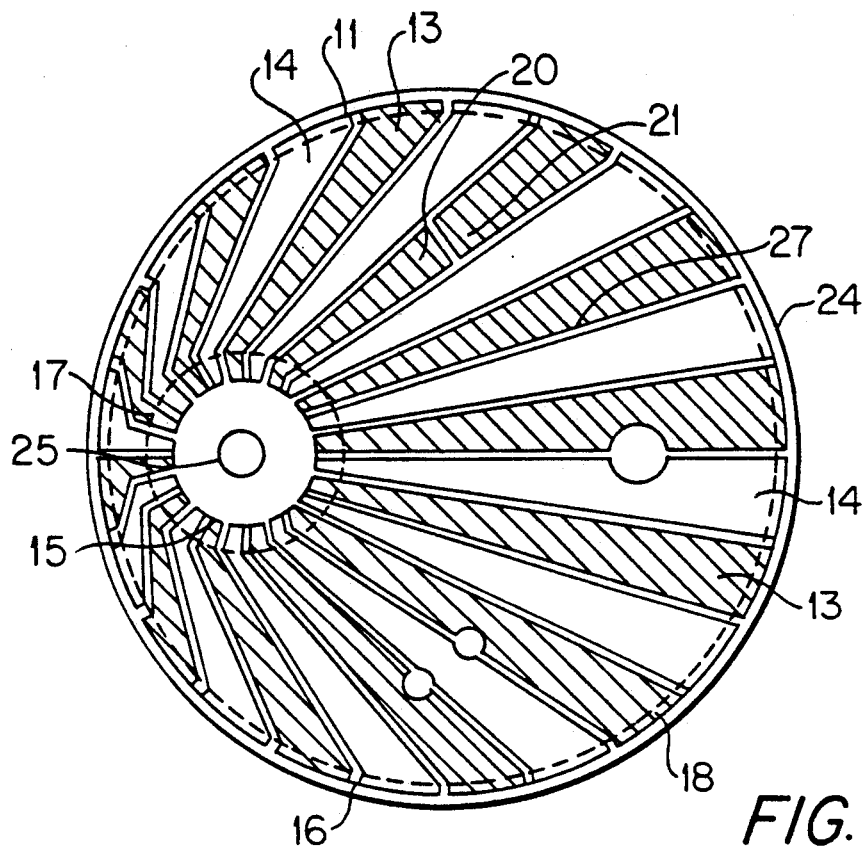
FIG. 3a is a schematic representation of the sample material thermopile of the differential thermal analysis sensor of the present invention applied to a substrate.

FIG. 3a shows the configuration of sample thermopile 11 as applied to a substrate using either thin film or thick film techniques, before an insulating layer and thermopile 12 are applied. Positive thermoelements 13 and negative thermoelements 14 are applied to the substrate in an alternating pattern of sectors extending from region 18 at the circumference of the substrate to the circular patterns defining region 17. The positive and negative thermoelement materials are separated by spaces 27, except for junctions 15 or 16 at each end of the thermoelements. Thus, at alternating ends of adjacent arc segments defining the circular measuring zone 17, the positive 13 and negative 14 thermoelements overlap to form measuring junctions 15. Similarly, at alternating ends of adjacent arc segments defining thermoelectric reference zone 18, the positive 13 and negative 14 thermoelements overlap to form thermoelectric reference junctions 16.

One of the positive thermoelement regions 13 is interrupted to form terminals 20 and 21 of thermopile 11. The sample temperature measuring thermocouple 25 is applied to that substrate at the center of measuring zone 17. Thus thermopile 11 can measure the difference in temperature between the sample measuring zone 17 formed by the circular pattern of measuring junctions 15 and the thermoelectric reference zone 18 formed by the circular pattern of reference junctions 16. The electrical impedance of this thermopile is inherently low because of the large cross-sectional area of thermoelements 13 and 14. This thermopile can function as a Peltier heat pump by application of a direct electrical current to terminals 20 and 21. Heat will be pumped in proportion to the magnitude of the applied direct current, in a direction determined by the direction of the current. Thus thermopile 11 can be used to transport heat from region 18 to the region 17, or from region 17 to region 18.

Figure 3B:
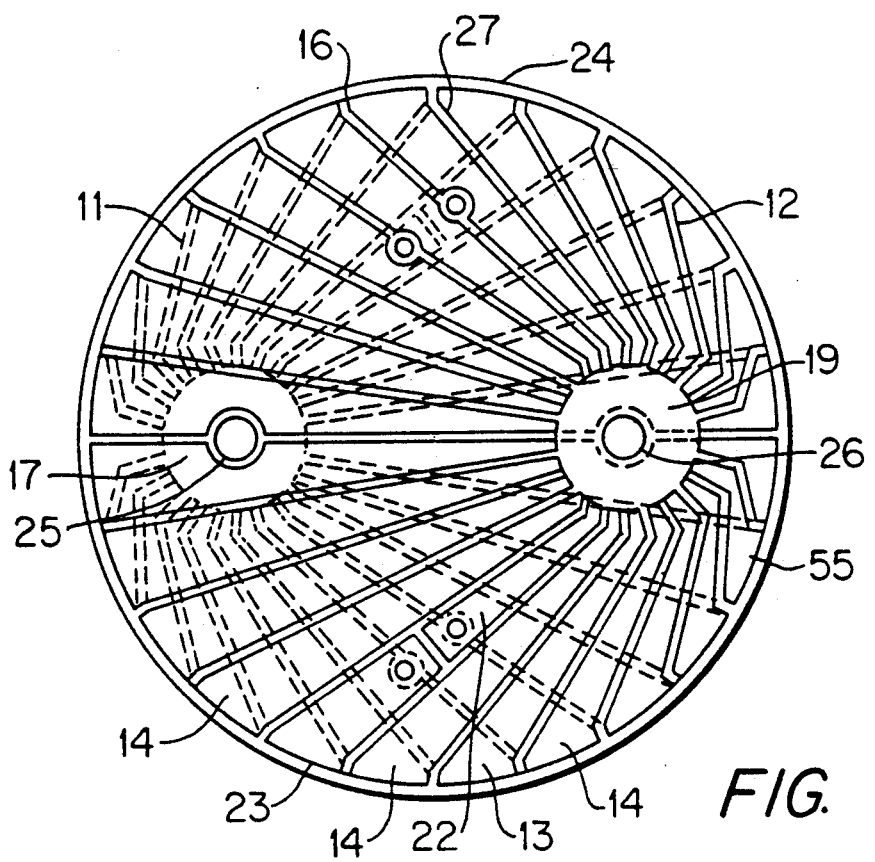
FIG. 3b is a schematic representation of the reference material thermopile of the differential thermal analysis sensor of the present invention applied to a substrate over the sample material thermopile.
Figure 3C:
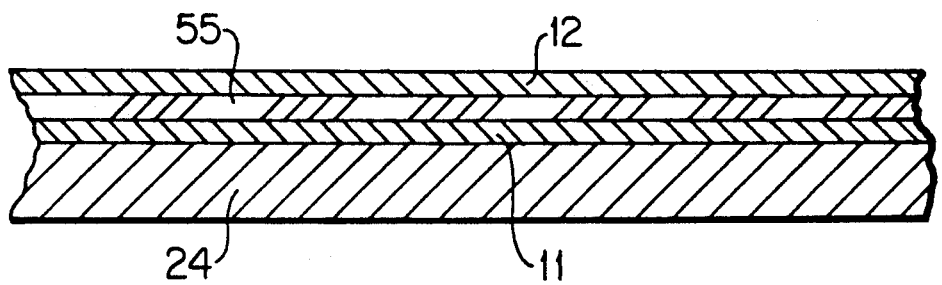
FIG. 3c is a schematic cross-section of the thermal analysis sensor of the present invention.

FIG. 3b shows the complete dual thermopile differential thermal analysis sensor. To fabricate the dual differential thermopile sensor, thermopile 12 is fabricated on substrate 24 over thermopile 11. Thermopile 11 is first covered with a layer of electrically insulating material 55 containing holes allowing for connection to thermopile 1 then thermopile 12 is applied over the insulating layer as shown in FIG. 3c. Thermopile 12 is aligned with thermopile 11 such that thermoelectric reference junctions 16 of thermopile 12 are positioned over thermoelectric reference junctions 16 of thermopile 11. Thermopile 12 is oriented such that measuring region 19 is diametrically opposed to measuring region 17 about the center of substrate 24. The insulating layer is formed with holes over the center of measuring region 17 and over terminals 20 and 21, such that electrical connections may be made to sample temperature thermocouple 25 and to terminals 20 and 21.

The material for substrate 24 must be selected for its heat transfer characteristics, thermal stability and resistance to corrosion. Differential scanning calorimetry depends upon the temperature difference created across the surface of the substrate as heat flows to (and from) the sample. The magnitude of the temperature difference created and the speed with which the temperature difference decays following termination of the heat flow determine the calorimetric sensitivity and the resolution, respectively, of the instrument. Both calorimetric sensitivity and instrument resolution depend on the thermal diffusively of the substrate material. The thermal diffusively of a material is its thermal conductivity divided by the product of its density and its specific heat. Sensors fabricated using substrates made from materials having high values of thermal diffusively will have relatively low sensitivity and high resolution. Sensors fabricated using substrates made from materials having low values of thermal diffusively will have relatively high sensitivity and relatively low resolution.

If the the implements forming thermopile 11 are applied directly to the substrate, the substrate must be an electrically insulating material, or if the substrate is electrically conductive, it must be coated with an electric insulating material before thermopile 11 is applied. Ceramic materials are preferred for use as substrates because they possess the requisite thermal stability and corrosion resistance, and exhibit a wide range of thermal diffusively. These materials are also well suited to the fabrication techniques required to form thermopiles 11 and 12. For example, zirconia ($ZrO_2$), which has very low thermal diffusively, would be suitable for fabricating a high-sensitivity (but low resolution) sensor. Beryllia (BeO), which has high thermal diffusively, could be used to fabricate a high-resolution (but low sensitivity) differential scanning calorimeter. Alumina ($Al_2O_3$) has moderate values of thermal diffusively and could be used to fabricate a device with intermediate sensitivity and resolution. These materials may have monocrystalline or polycrystalline structures. Polycrystalline materials are most often used, although single crystal alumina, i.e., sapphire, might be used because of its chemical inertness. Amorphous materials such as fused silica ("quartz glass") could also be used as substrates.

For example, a sample of material exhibiting a change of phase (such as a melt transition) is loaded in a sample pan and placed on the sample position. An empty pan is placed on the reference position. The temperature of the enclosure is increased linearly. The record of the difference between sample material temperature and reference material temperature versus sample material temperature is shown in FIG. 4.

Figure 4:
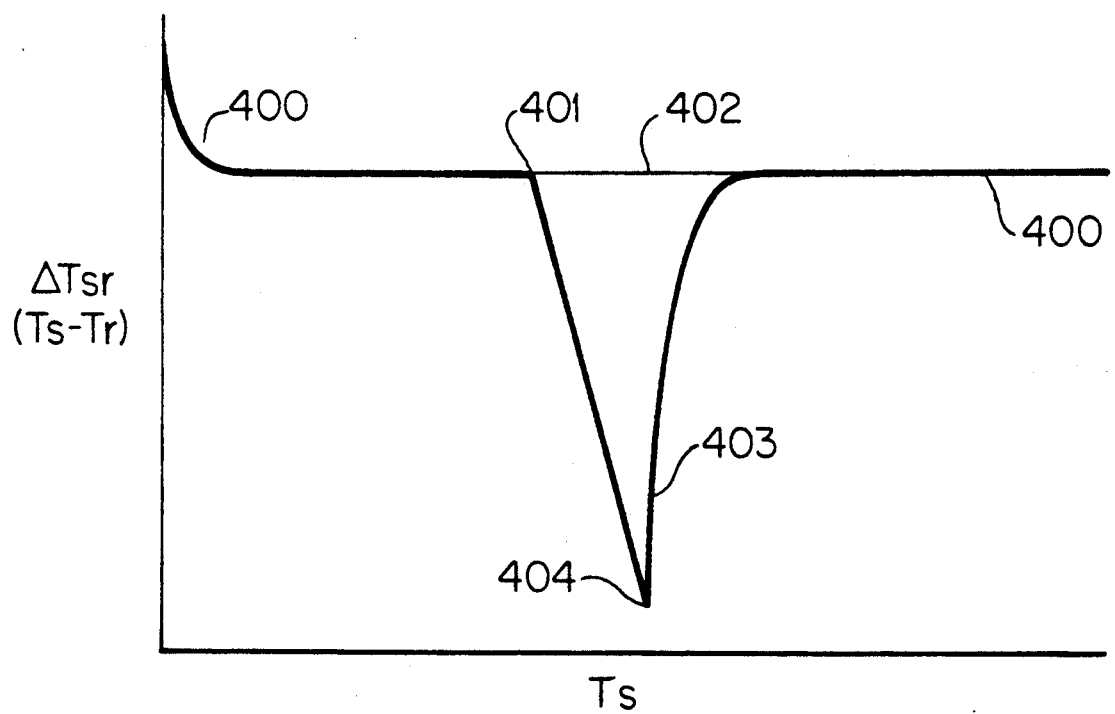
FIG. 4 shows the difference between the sample material temperature and the reference material temperature for a first order transition such as a melt in a single-sample heat flux differential calorimeter.

The onset of the transition 401 shown in FIG. 4 corresponds to the melting temperature. The area between the $\Delta T_{sr}$ curve 400 and the transition baseline 402 is a measure of the total heat of transition. Peak 404 is the termination of the transition. The peak height is proportional to the maximum difference between the temperatures of the sample and reference materials, and to the number of thermocouples in each thermopile. The peak height is thus a measure of the calorimetric sensitivity of the instrument. The duration of the post transition recovery 403 is a measure of the resolution of the instrument (faster return to baseline indicates higher resolution). The direction of the peak indicates the direction of heat flow. Negative temperature differences indicate endothermic transitions, and positive temperature differences indicate exothermic transitions.

Dual Thermopile Reat Flux Differential Scanning Calorimeter

Figure 5:
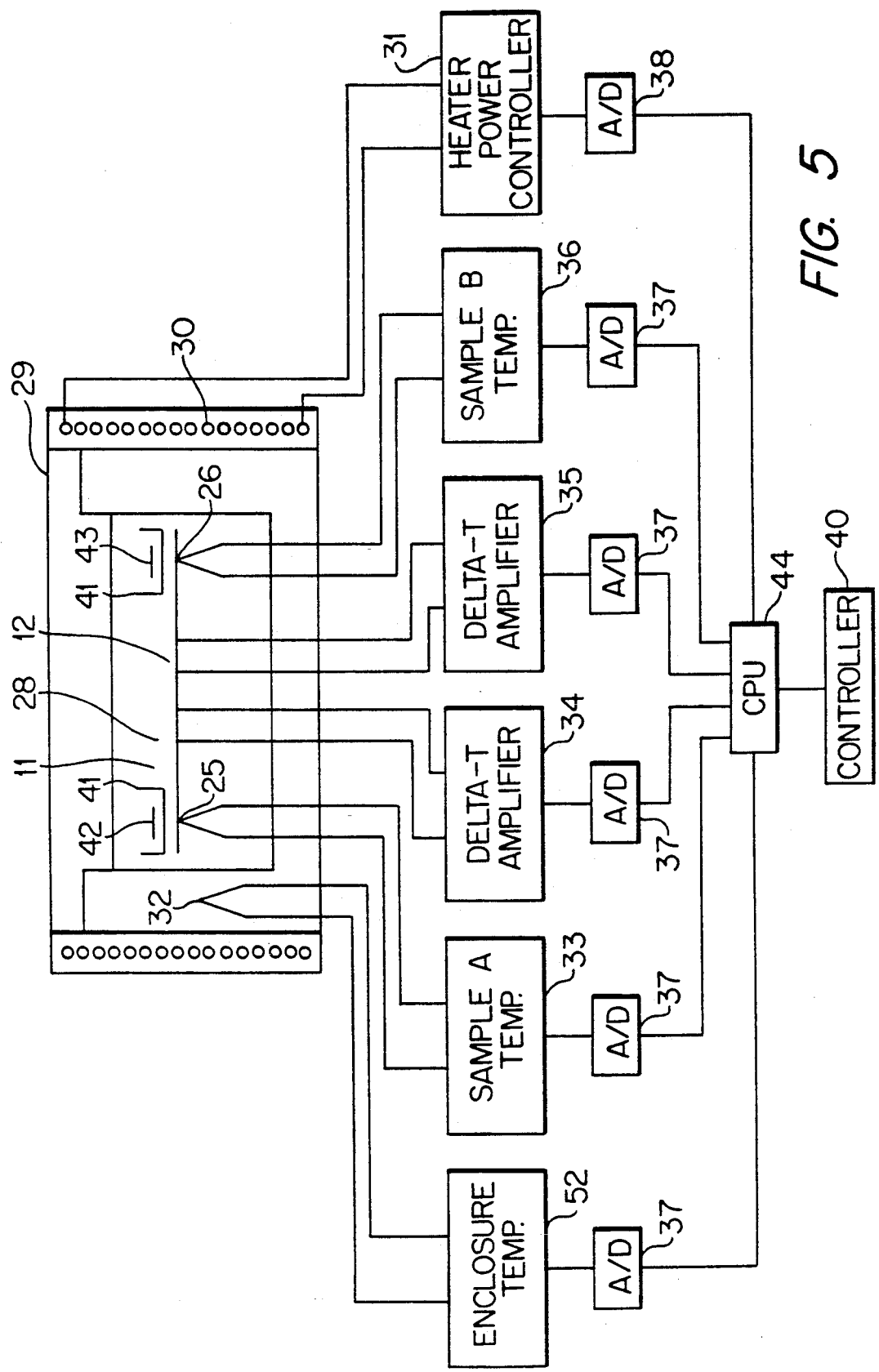
FIG. 5 is a schematic block diagram representation of a dual thermopile heat flux Differential Scanning Calorimeter.

FIG. 5 shows the dual thermopile thermal analysis sensor in a heat flux differential scanning calorimeter system. The dual thermopile thermal analysis sensor 28 is installed in a regulated temperature enclosure 29 which includes an electrical resistance heating element 30. The temperature of the enclosure 29 is monitored by a thermocouple 32 mounted within the body of the enclosure.

The electrical output of thermocouple 32 is input to a temperature amplifier 52 which includes compensation for the thermocouple cold junction. The output from the temperature amplifier is fed to an analog to digital converter 37. The output of analog to digital converter 37 is fed to instrument central processing unit (CPU) board 44. Temperature amplifier 52 is a DC electronic amplifier which amplifies the signals produced by thermocouple 32. In a similar manner, the electrical output of each of the measuring region thermocouples 25 and 26 are fed to temperature amplifiers 33 and 36. The outputs of temperature amplifiers 33 and 36 are fed to analog to digital converters 37. The outputs of analog to digital converters 37 are then fed to CPU board 44. Differential temperature signals from thermopiles 11 and 12 are fed to differential temperature amplifiers 34 and 35. Signals from the differential temperature amplifiers 34 and 35 are fed to analog to digital converters 37 and then to CPU board 44.

Enclosure heating element 30 is supplied variable alternating electrical currents from heater power controller 31 which obtains its drive signal from CPU board 44 and returns a measure of the output current to instrument CPU board 44 through analog to digital converter 38. CPU board 44 communicates via a digital signal bus to instrument controller 40. Instrument controller 40 is a separate computer which can provide programs e.g., thermal programs, to CPU board 44 and can analyze the data obtained. The sample and/or reference materials 42 and 43 (depending upon whether single or dual-sample mode is in use) are loaded into pans 41 which are installed on measuring zones 17 and 19 of the differential thermal analysis sensor 28.

Instrument CPU board 44 contains hardware and software programs to control the instrument and to store and process the signals obtained from experimental runs. The temperature enclosure 29 is controlled by comparison of the enclosure temperature with the temperature program setpoint value within CPU board 44. Based on the difference between the reassured enclosure temperature and the desired program value, a discrete proportional plus integral plus derivative control algorithm generates a desired power signal for the heater power controller 31. A signal indicating the power supplied by heater power controller 31 is fed back to CPU board 44, thus forming a closed loop programmable temperature controller. During an experimental run the enclosure temperature and the sample temperature(s) are stored within CPU board 44. The signals which arrive at CPU board 44 from the differential thermopiles are combined as required by the operating mode. CPU board 44 also calculates and stores the heat flow to and from the sample materials. These stored data sets are then retrieved, analyzed and displayed by instrument controller 40.

Dual Thermopile Power Compensated Differential Scanning Calorimeter

Figure 6:
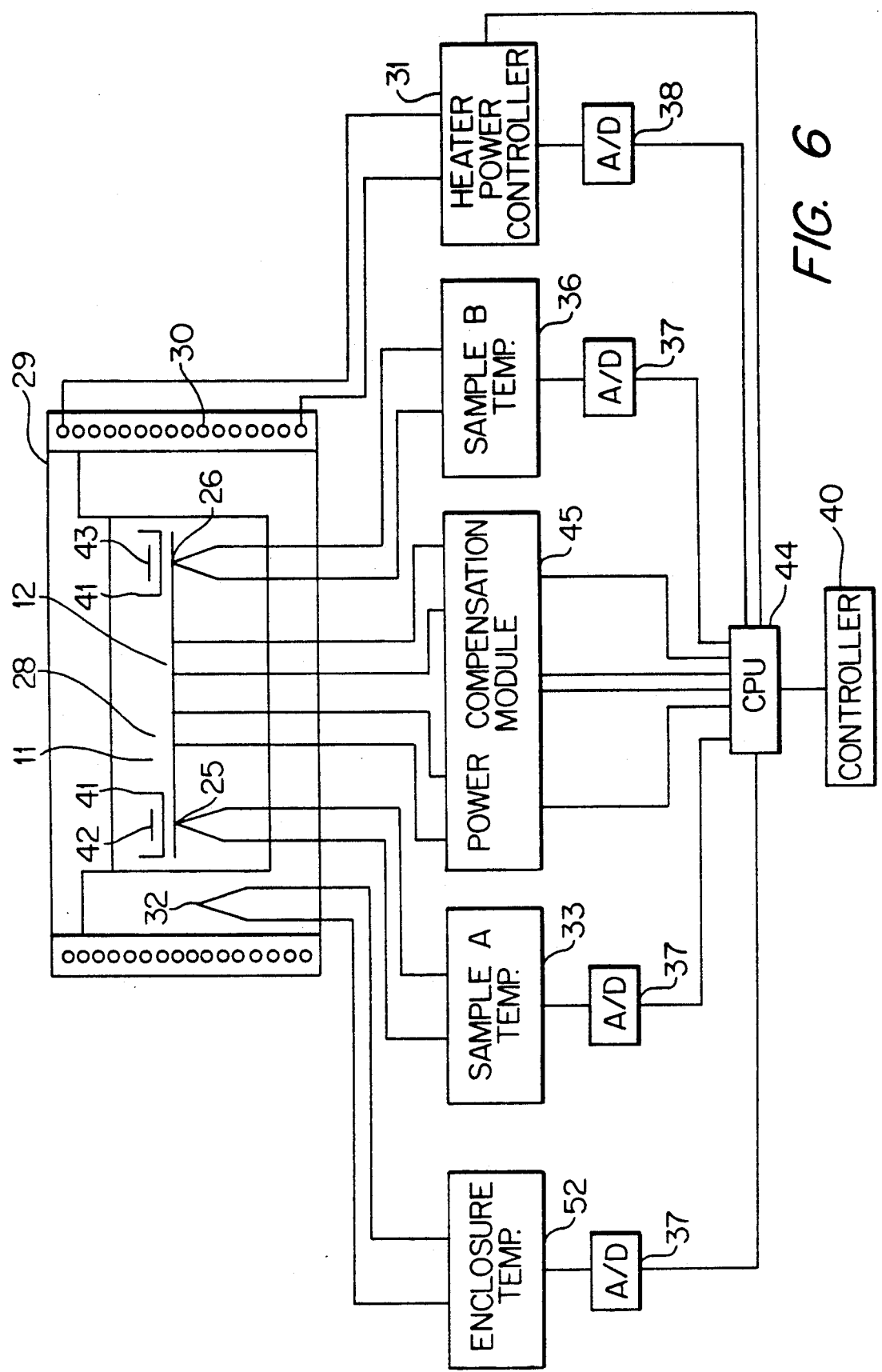
FIG. 6 is a schematic block diagram representation of a dual thermopile power compensation Differential Scanning Calorimeter.

FIG. 6 shows the dual thermopile thermal analysis sensor in a power compensated differential scanning calorimeter system. The dual thermopile thermal analysis sensor 28 is installed in a regulated temperature enclosure 29 which includes an electrical resistance heating element 30. The temperature of the enclosure 29 is monitored by a thermocouple 32 mounted within the body of the enclosure.

The electrical output of thermocouple 32 is input to a temperature amplifier 52 which includes compensation for the thermocouple cold junction. The output from the temperature amplifier is fed to an analog to digital converter 37. The output of analog to digital converter 37 is fed to instrument central processing unit board 44. In a similar manner, the electrical output of each of the measuring region thermocouples 25 and 26 are fed to temperature amplifiers 33 and 36. The outputs of temperature amplifiers 33 and 36 are fed to analog to digital converters 37. The outputs of analog to digital converters 37 are then fed to the CPU board 44. Differential temperature signals from thermopiles 11 and 12 are fed to the power compensation module 45.

Enclosure heating element 30 is supplied variable alternating electrical currents from heater power controller 31 which obtains its drive signal from the CPU board 44 and returns a measure of the output power to the instrument central processing unit board 44 through an analog to digital converter 38. CPU board 44 communicates via a digital signal bus to instrument controller 40. Instrument controller 40 is a separate computer which can provide programs, e.g., thermal programs, to CPU board 44, and can analyze the data obtained. The sample and/or reference materials 42 and 43 (depending upon whether single or dual-sample mode is in use) are loaded into pans 41 which are installed on measuring zones 17 and 19 of the differential thermal analysis sensor 28.

Figure 7:
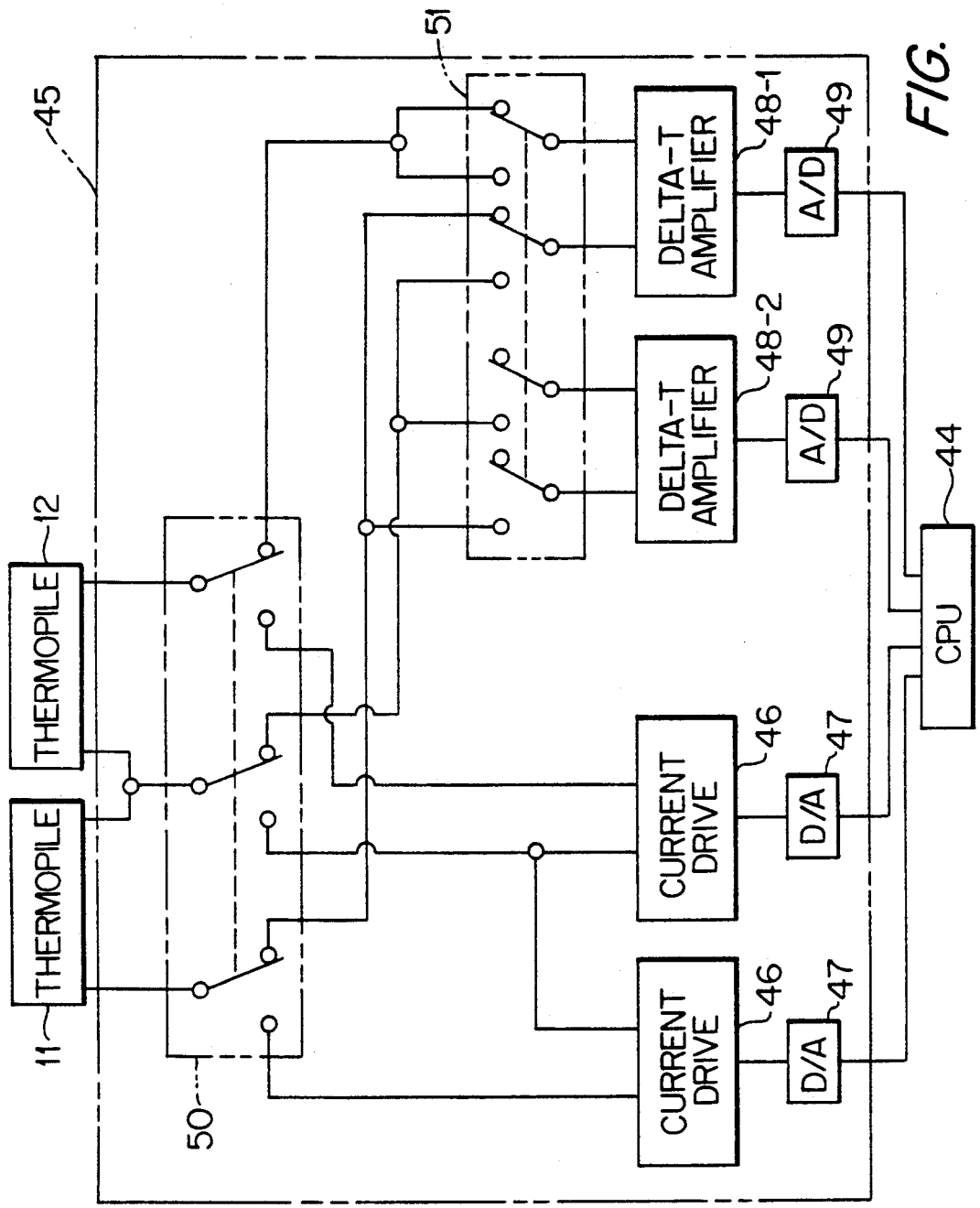
FIG. 7 is a schematic block diagram representation of a power compensation module of a dual thermopile power compensated differential scanning calorimeter.

FIG. 7 shows the configuration of the power compensation module 45. Thermopiles 11 and 12 are connected to the multiplexer 50 which allows the thermopiles to be used alternately for differential temperature measurements or for power compensation, i.e., as heat pumps employing the Peltier effect. As shown, multiplexer 50 connects thermopiles 11 and 12 to mode selector 51 which in turn connects the thermopile outputs to differential temperature amplifiers 48-1 and 48-2. Mode selector switch 51 is used to configure the instrument as a single or dual-sample power compensation differential scanning calorimeter. As shown, the single-sample mode is selected. In the single-sample mode, the two thermopiles 11 and 12 are connected in series during the differential temperature measuring portion of the multiplexer cycle, providing a measure of the temperature difference between sample and reference regions 17 and 19. Differential temperature amplifier 48-2 is not used. In the dual-sample mode the selector switch 51 connects each of thermopiles 11 and 12 individually to differential temperature amplifiers 48-1 and 48-2 during the differential temperature measuring portion of the multiplexer cycle.

The output from the differential temperature amplifier(s) is evaluated by a power compensation control program in the CPU which seeks to null the temperature difference(s) measured on the sensor by varying the Peltier currents supplied to the thermopile. The power compensation control program contains a discrete proportional plus integral plus derivative control algorithm which generates a correction signal for the Peltier current supplies 46. The correction signals are fed via digital-to-analog converters 47 to Peltier current supplies 46. Multiplexer 50, when in the alternate position to the position shown in FIG. 7, connects the Peltier current supplies 46 to the thermopiles 11 and 12, enabling the thermopiles to function as Peltier heat pumps. The multiplexer alternately connects the thermopiles 11 and 12 to the differential temperature amplifiers 48-1 and 48-2 or to the Peltier current supplies 46. In operation the thermopiles will be connected to the Peltier current supplies 46 for a proportionally greater period of time than to the differential temperature amplifiers 48-1 and 48-2.

The power compensated differential scanning calorimeter described above may be used to perform single-sample or dual-sample measurements. Operation in the single-sample mode comprises loading a sample material 42 in pan 41 which is placed on sensor measuring region 17. An inert reference material 43 is placed in pan 41 which is placed on sensor measuring region 19. In some cases, however, the reference material may be omitted. The temperature control program is executed, and the current signals from Peltier current supplies 46 and the sample temperature from thermocouple 25 are stored in the CPU board. The difference in the Peltier currents supplied to the sample and reference thermopiles 11 and 12 is proportional to the flow of heat to and from the sample material 42. Operation in dual-sample mode consists of loading inert reference materials into pans 41 which are placed on both measuring regions 17 and 19. The temperature control program is executed, the current signals from Peltier current supplies 46 and the reference temperatures from thermocouples 25 and 26 are stored in the CPU board. Next, sample materials are loaded into pans 41 which are placed on both measuring regions 17 and 19. The temperature control program is executed, and the current signals from Peltier current supplies 46 and the sample temperatures from thermocouples 25 and 26 are stored in the CPU board. The differences between the Peltier currents supplied to the thermopiles 11 and 12 during the sample run and the Peltier currents supplied to the thermopiles 11 and 12 during the reference run are proportional to the flow of heat to and from the two sample materials. The reference run need only be executed once, after which multiple sample runs may be executed.

Instrument CPU board 44 contains software programs and hardware to control the instrument and to store and process the signals obtained. The temperature of enclosure 29 is controlled by comparing the enclosure temperature signal with the temperature program setpoint value, within CPU board 44. Based on the difference between the measured enclosure temperature and the desired program value, a discrete proportional plus integral plus derivative control algorithm generates a desired power signal which is fed to heater power controller 31. A signal indicating the power supplied by heater power controller 31 is fed back to CPU board 44, thus forming a closed loop programmable temperature controller. During an experimental run, the enclosure temperature and the sample and/or reference temperatures are stored within CPU board 44. The current drive signals generated by CPU board 44 are combined in a suitable manner depending upon the operating mode and calculations of heat flow to and from samples are made and stored. These stored data sets may be retrieved, analyzed, plotted and displayed by instrument controller 40.

Dual Thermopile Power Compensated Differential Scanning Calorimeter—Alternate Construction An alternate way of using the dual thermopile power compensated differential scanning calorimetry sensor described above is to add two differential thermocouples or thermopiles to the sensor to continuously reassure the temperature difference between each of the measuring regions 17 and 19 and the reference region 18. The multiplexing arrangement described above is thus eliminated, and the thermopiles are used alternately as Peltier heat pumps and differential temperature sensors.

Figure 8:
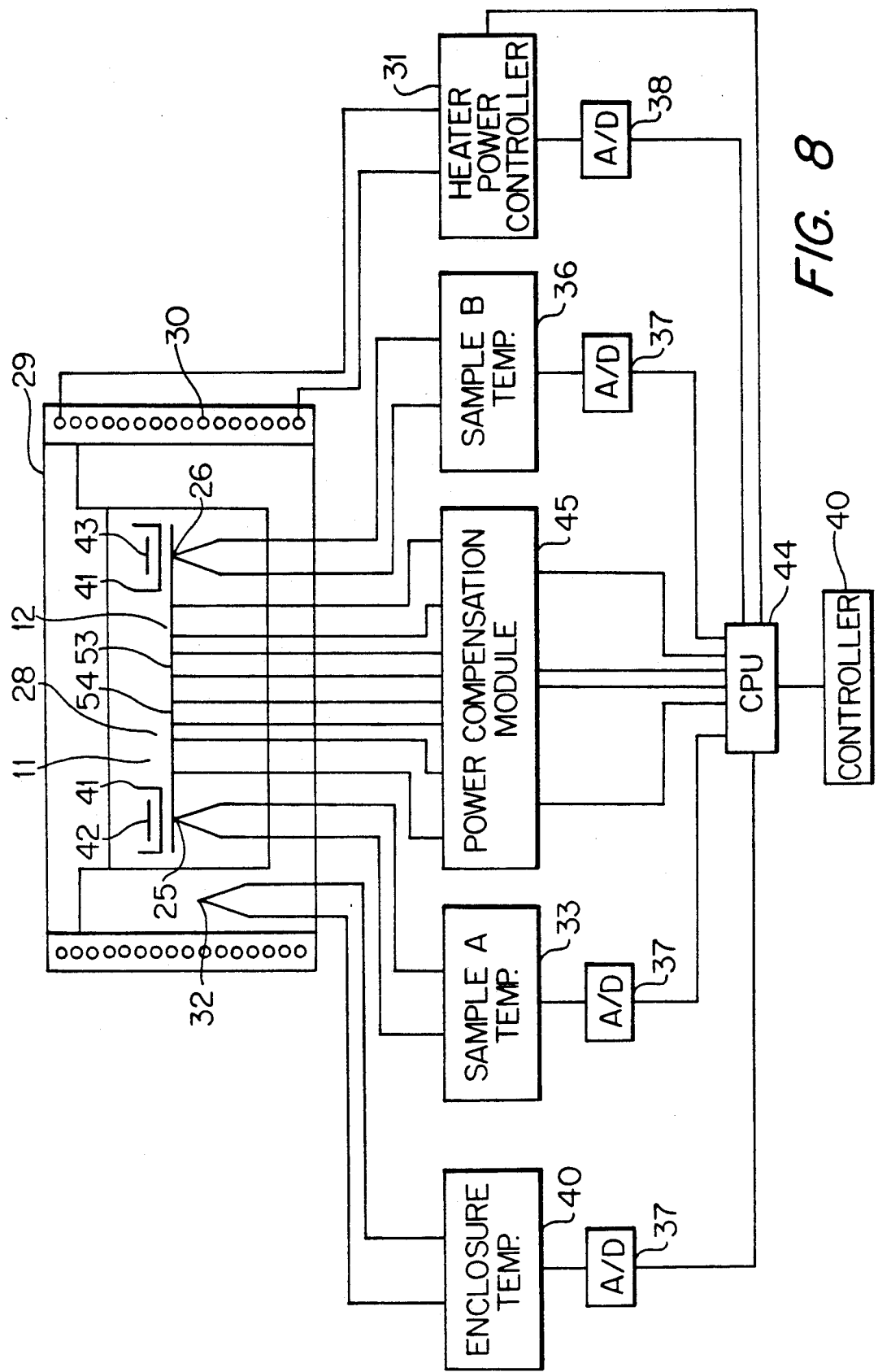
FIG. 8 is a schematic diagram of an alternate dual thermopile thermal analysis sensor.
Figure 9:
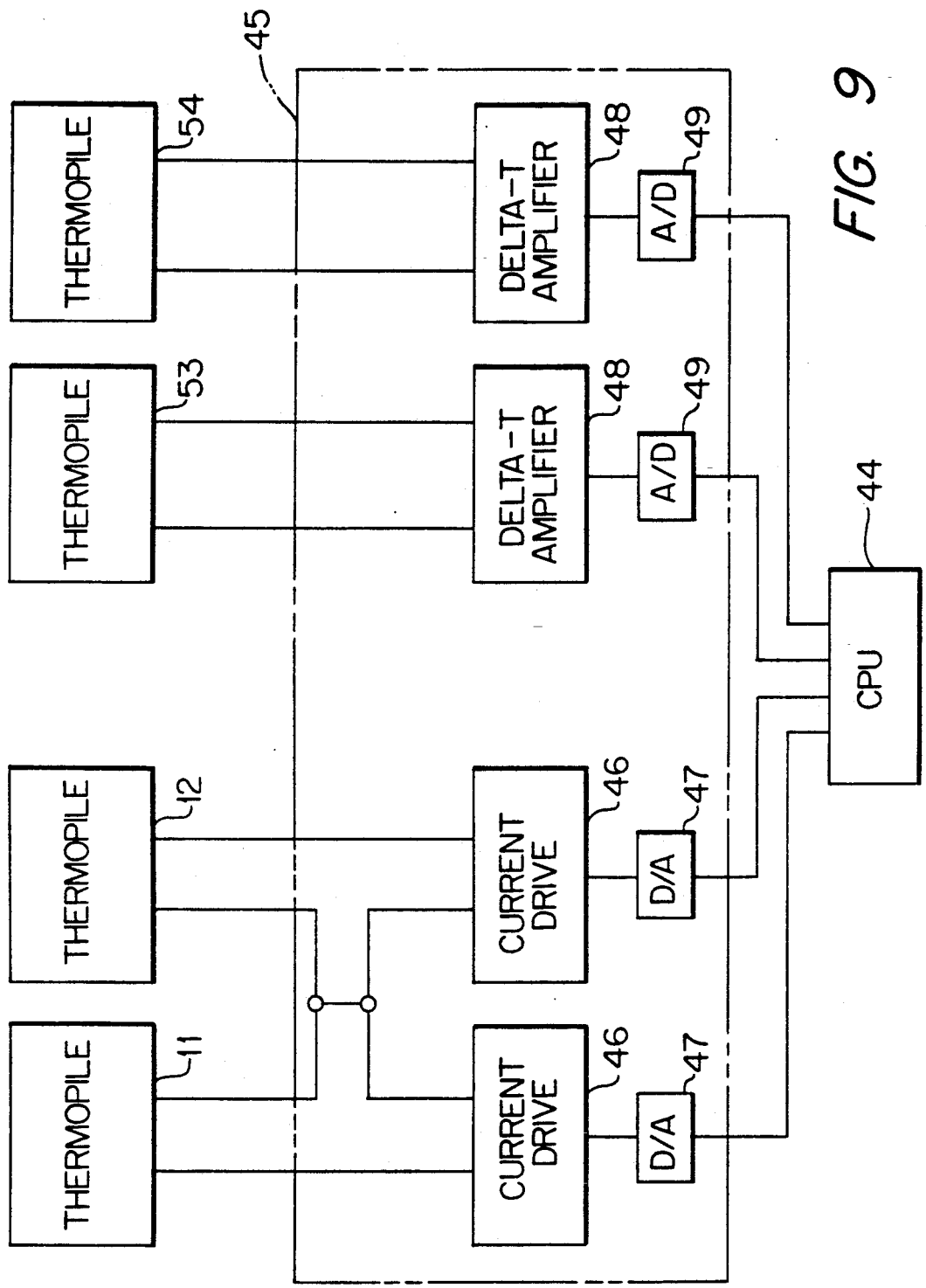
FIG. 9 is a schematic representation of the power compensation module used with the sensor of FIG. 8.

As shown in FIGS. 8 and 9, a third thermopile 53 is attached, over an electrical insulating layer, to the dual thermopile differential thermal analysis sensor 28 over thermopiles 11 and 12. Thermopile 53 has the same orientation as thermopile 11, and a similar configuration. However, it does not necessarily have the same number of measuring junctions and thermoelectric reference junctions. Thermopile 53 thus provides a measure of the temperature difference between measuring region 17 and reference temperature region 18. A fourth thermopile 54 is then attached, over another electrical insulating layer, to the dual thermopile differential thermal analysis sensor 28 over thermopile 53. Thermopile 54 has the same orientation as thermopile 12 and a similar configuration. However, like thermopile 53, it may be constructed using a different number of measuring junctions and thermoelectric reference junctions. Thermopile 54 thus provides a measure of the temperature difference between measuring region 19 and reference temperature region is. Differential temperature measuring thermocouples may be substituted for thermopiles 53 and 54.

FIG. 8 shows the alternate dual thermopile thermal analysis sensor as incorporated into a power compensation differential scanning calorimeter system. The dual thermopile thermal analysis sensor 28 is installed in a regulated temperature enclosure 29 which includes an electrical resistance heating element 30. The temperature of the enclosure 29 is monitored by a thermocouple 32 mounted within the body of the enclosure. The electrical output of the thermocouple 32 is input to a temperature amplifier 40 which includes thermocouple cold junction compensation. The output from the temperature amplifier is fed to analog to digital converter 37 and finally to instrument CPU board 44. In a similar manner, the electrical output of each of the measuring region thermocouples 25 and 26 are fed to temperature amplifiers 33 and 36, the outputs of which are fed to analog to digital converters 37. These outputs are in turn fed to CPU board 44. The differential temperature signal from thermopiles 53 and 54 are fed to power compensation module 45.

Enclosure heating element 30 is supplied variable alternating electrical currents from heater power controller 31. Power controller 31 obtains its control signals from CPU board 44, and returns a measure of its output power to CPU board 44 through analog to digital converter 38. CPU board 44 is connected via a digital signal bus to instrument controller 40. Instrument controller 40 is a separate computer which provides means to supply experiment programs (essentially the thermal programs) to CPU board 44 and means to analyze data obtained from an experimental run. The sample and/or reference materials 42 and 43 (depending upon whether single or dual-sample mode is in use) are loaded into pans 41 which are installed on measuring zones 17 and 19 (not shown) of the differential thermal analysis sensor 28. Instrument CPU board 44 contains the hardware and software required to facilitate instrument control, and to process and store the signals obtained from experimental runs.

The temperature of enclosure 29 is controlled by comparing, within CPU board 44, the enclosure temperature signal with the temperature program setpoint value. Based on the difference between the measured enclosure temperature and the desired program value, a discrete proportional plus integral plus derivative control algorithm generates a desired power signal which is fed to the heater power controller 31. A signal indicating the power supplied by the heater power controller 31 is fed back to the CPU board, thus forming a closed loop programmable temperature controller.

During an experimental run, the enclosure, sample and/or reference temperatures are stored within the CPU board. The current drive signals generated by the CPU board are combined in a suitable manner depending upon the operating mode and how calculations of heat flow to and from samples are made and stored. These stored data sets may be retrieved by the instrument controller and subjected to a variety of analytical routines which give the analyst the desired experimental results.

FIG. 9 shows the configuration of the power compensation module 45. Thermopiles 11 and 12 are connected to Peltier current supplies 46, which receive control signals from CPU board 44 via the digital to analog converters 47. The outputs of thermopiles 53 and 54 are fed to differential temperature amplifiers 48 which are connected to analog to digital converters 49 which are connected to CPU board 44. The output from the differential temperature amplifiers is evaluated by a power compensation control program in the CPU which seeks to null the temperature difference measured by thermopiles 53 and 54 by varying the Peltier currents supplied to the thermopiles 11 and 12. As shown by FIG. 9, the power-compensation control program contains a discrete proportional plus integral plus derivative control algorithm which generates correction signals for the Peltier current supplies 46. The correction signals are fed via digital to analog converters 47 to the Peltier current supplies 46.

The power compensated differential scanning calorimeter described above may be used to perform single-sample or dual-sample experiments. Operation in single-sample mode consists of loading a sample material 42 in pan 41 which is placed on sensor measuring region 17. An inert reference material 43 is also placed in pan 41 which is placed on sensor measuring region 19. (Alternately, the reference material may be omitted.) The temperature control program is executed, and the current signals from Peltier current supplies 46 and the sample temperature from thermocouple 25 are stored in the CPU board. The difference in the Peltier currents supplied to the sample and reference thermopiles 11 and 12 is proportional to the flow of heat to and from sample material 42.

operation in dual-sample mode consists of loading inert reference materials into pans 41 which are placed on both reassuring regions 17 and 19. The temperature control program is executed, and the current signals from Peltier current supplies 46 and the reference temperatures from thermocouples 25 and 26 are stored in the CPU board. Next, sample materials are loaded into pans 41 which are placed on both measuring regions 17 and 19. The temperature control program is executed, and the current signals from Peltier current supplies 46-and the sample temperatures from thermocouples 25 and 26 are stored in the CPU board. The differences between the Peltier currents supplied to thermopiles 11 and 12 during the sample run and the Peltier currents supplied to thermopiles 11 and 12 during the reference run are proportional to the flow of heat to and from the two sample materials. The reference run need only be executed once, after which multiple sample runs may be executed.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A differential thermal analysis sensor comprising:
   (a) a substrate having a surface;
   (b) a first thermopile attached to said surface of said substrate, said first thermopile having a first set of measuring junctions positioned around a first measuring zone, and a first set of thermoelectric reference junctions, wherein said first set of thermoelectric reference junctions are attached to the substrate, said first thermopile being characterized by a low electrical impedance;
   (c) a second thermopile attached to said surface of said substrate, said second thermopile having a second set of measuring junctions positioned around a second measuring zone, and a second set of thermoelectric reference junctions, said second thermopile also being characterized by a low electrical impedance; and
   (d) a first layer of insulating material electrically insulating said first thermopile from said second thermopile, wherein said second set of thermoelectric reference junctions are attached to said first layer of insulating material, and wherein
   the thermoelectric reference junctions of said first thermopile and the thermoelectric reference junctions of said second thermopile are positioned in a common reference zone.

2. The differential thermal analysis sensor of claim 1, wherein the first and second thermopiles are each comprised of in-series thermocouples, said thermocouples being comprised of thermoelements fabricated using thin film techniques.

3. The differential thermal analysis sensor of claim 1, wherein the first and second thermopiles are each comprised of in-series thermocouples, said thermocouples being comprised of thermoelements fabricated using thick film techniques.

4. The differential thermal analysis sensor of claim 1, wherein the substrate is a high thermal diffusivity material, such that the sensor is characterized by having a high resolution.

5. The differential thermal analysis sensor of claim 1, wherein the measuring junctions of the first and second thermopiles are equally spaced in a circular pattern around the first and second measuring zones, respectively.

6. The differential thermal analysis sensor of claim 1, wherein the common reference zone is a circular region surrounding the measuring junctions, and the thermoelectric reference junctions are arranged in a circular pattern in the common reference zone.

7. The differential thermal analysis sensor of claim 1, wherein the substrate is circular.

8. The differential thermal analysis sensor of claim 7, wherein the centers of the first and second measuring zones are symmetrically positioned on a diameter of the circular substrate on either side of the center of the circular substrate.

9. The differential thermal analysis sensor of claim 1, further comprising a first thermocouple for measuring the temperature of the first measuring zone, and a second thermocouple for measuring the temperature of the second measuring zone.

10. The differential thermal sensor of claim 1, wherein the substrate has a low thermal diffusivity, such that the sensor is characterized by having very high calorimetric sensitivity.

11. The differential thermal analysis sensor of claim 1, wherein the substrate has a moderate thermal diffusivity, such that the sensor is characterized by having high calorimetric sensitivity.

12. A heat flux differential scanning calorimetry method comprising:
   (a) providing a differential temperature sensor in an enclosure, said differential temperature sensor comprising two low electrical impedance thermopiles applied to a single substrate, each thermopile having a set of measuring junctions and a set of thermoelectric reference junctions, the measuring junctions of each thermopile being positioned in its own separate measuring zone, and the thermoelectric reference junctions of the two thermopiles being attached to the substrate in a reference zone common to the two thermopiles;
   (b) placing a reference material on one measuring zone and a sample on the other measuring zone;
   (c) controlling the temperature of the enclosure according to a predetermined heating rate program;
   (d) combining the output of the two thermopiles; and
   (e) recording the difference in the temperature of the sample material and the reference material as a function of the temperature of the sample.

13. The heat flux differential scanning calorimetry method of claim 12, further comprising:
   (f) plotting the difference in the temperature of the sample material and the reference material as a function of the temperature of the sample;
   (g) identifying at least one transition;
   (h) determining the baseline for at least one of the transitions identified in step (g); and
   (i) determining the total heat of transition of the at least one transition.

14. The heat flux differential scanning calorimetry method of claim 12, wherein the substrate has a moderate thermal diffusivity, such that the sensor is characterized by having high calorimetric sensitivity.

15. The heat flux differential scanning calorimetry method of claim 12, wherein the substrate is a high thermal diffusivity material, such that the sensor is characterized by having a high resolution.

16. The heat flux differential scanning calorimetry method of claim 12, wherein the substrate is a high thermal diffusivity material, such that the sensor is characterized by having a high resolution.

17. A dual-sample heat flux differential scanning calorimetry method comprising:
   (a) providing a differential temperature sensor in an enclosure, said differential temperature sensor comprising two low electrical impedance measuring thermopiles applied to a single substrate, each thermopile having a set of measuring junctions and a set of thermoelectric reference junctions, the measuring junctions of each thermopile being positioned in its own separate measuring zone, and the thermoelectric reference junctions of the two thermopiles being attached to the substrate in a reference zone common to the two thermopiles;
   (b) placing a reference material on each measuring zone;
   (c) controlling the temperature of the enclosure according to a predetermined heating rate program;
   (d) recording the output of the two thermopiles;
   (e) placing a sample material on each measuring zone;
   (f) controlling the temperature of the enclosure according to the predetermined heating rate program;
   (g) recording the output of the two thermopiles;
   (h) separating the signals of the two reference materials;
   (i) separating the signals of the two sample materials; and
   (j) combining the results of each sample material measurement with the results of its respective reference material measurement to obtain heat flux data for each sample with respect to its respective reference material,
   wherein step (H) may be performed any time after step (d) and before step (j), and step (i) may be performed any time after step (g) and before step (j).

18. The heat flux differential scanning calorimetry method of claim 17, wherein the substrate has a moderate thermal diffusivity, such that the sensor is characterized by having high calorimetric sensitivity.

19. The heat flux differential scanning calorimetry method of claim 17, further comprising:
   (k) plotting the heat flux data as a function of the temperature of the sample material to obtain a plot of the heat flux as a function of temperature for each sample material;
   (l) identifying at least one transition in each plot;
   (m) determining the baseline for at least one of the transitions identified in-step (k); and
   (n) determining the total heat of transition of the at least one transition.

20. The heat flux differential scanning calorimetry method of claim 17, wherein the substrate is a high thermal diffusivity material, such that the sensor is characterized by having a high resolution.

21. The heat flux differential scanning calorimetry method of claim 17, wherein the substrate is a high thermal diffusivity material, such that the sensor is characterized by having a high resolution.

22. A power compensated differential scanning calorimetry method comprising:
   (a) providing a differential temperature sensor in an enclosure, said differential temperature sensor comprising two thermopiles applied to a single substrate such that each thermopile has an independent temperature controlled zone, and a heat source/sink zone which is common to both thermopiles, said differential temperature sensor including thermocouples for measuring the temperature of each of the temperature controlled zones, each thermopile having a set of temperature-controlling junctions and a set of heat source/sink junctions, the temperature-controlling junctions of each thermopile being positioned in its own separate temperature-controlling zone, and the heat source/sink junctions of the two thermopiles being attached to the substrate in a heat source/sink zone common to the two thermopiles;
   (b) placing a sample material on one of the temperature controlled zones and a reference material on the other temperature controlled zone;
   (c) controlling the temperature of the enclosure according to a predetermined heating rate program;
   (d) independently supplying direct current electrical currents to each of the thermopiles such that the thermopiles pump heat to and from the heat source/sink regions to the temperature controlled region such that the temperature difference between the sample and reference materials is suppressed; and (e) measuring and recording the direct current electrical currents supplied to each of the thermopiles.

23. The power compensated differential scanning calorimetry method of claim 22, wherein the substrate has a moderate thermal diffusivity, such that the sensor is characterized by having high calorimetric sensitivity.

24. The power compensated differential scanning calorimetry method of claim 22, further comprising:
 (f) calculating the heat flow to the sample material;
 (g) calculating the heat flow to the reference material;
 (h) plotting the difference between the heat flow to the sample material and the heat flow to the reference material as a function of the temperature of the sample to obtain a heat flow plot;
 (i) identifying at least one transition in the heat flow plot;
 (h) determining the baseline for at least one of the transitions identified in step (i); and
 (j) determining the total heat of transition of the at least one transition.

25. The power compensated differential scanning calorimetry method of claim 22, wherein the substrate is a high thermal diffusivity material, such that the sensor is characterized by having a high resolution.

26. The power compensated differential scanning calorimetry method of claim 22, wherein the substrate is a high thermal diffusivity material, such that the sensor is characterized by having a high resolution.

27. A dual sample power compensated differential scanning calorimetry method comprising:
 (a) providing a differential temperature sensor in an enclosure, said differential temperature sensor comprising a first and a second thermopile applied to a single substrate such that the first thermopile has a first independent temperature controlled zone and the second thermopile has a second independent temperature controlled zone, and a heat source/sink zone which is common to both thermopiles, said differential temperature sensor including a first thermocouple for measuring the temperature of the first temperature controlled zone and a second thermocouple for measuring the temperature of the second temperature controlled zone, each thermopile having a set of temperature-controlling junctions and a set of heat source/sink junctions, the temperature-controlling junctions of each thermopile being positioned in its own separate temperature-controlling zone, and the heat source/sink junctions of the two thermopiles being attached to the substrate in a heat source/sink zone common to the two thermopiles;
 (b) placing a first reference material on the first temperature controlled zone and a second reference material on the second temperature controlled zone;
 (c) controlling the temperature of the enclosure according to a predetermined heating rate program;
 (d) independently supplying direct current electrical currents to the first thermopile and to the second thermopile such that the first and second thermopiles pump heat to and from the heat source/sink regions to the temperature controlled region such that the temperature difference measured by the first thermocouple and the second thermocouple is suppressed;
 (e) measuring and recording the direct current electrical current supplied to the first thermopile and the direct current electrical current supplied to the second thermopile
 (f) placing a first sample material on the first temperature controlled zone and a second sample material on the second temperature controlled zone;
 (g) controlling the temperature of the enclosure according to the predetermined heating rate program;
 (h) independently supplying direct current electrical currents to the first thermopile and to the second thermopile such that the first and second thermopiles pump heat to and from the heat source/sink regions to the temperature controlled region such that the temperature difference measured by the first thermocouple and the second thermocouple is suppressed;
 (i) measuring and recording the direct current electrical current supplied to the first thermopile and the direct current electrical current supplied to the second thermopile;
 (j) combining the results of the sample material measurement with the results of the first reference material measurement to obtain heat flux data for the first sample with respect to the first reference material; and
 (k) combining the results of the second sample material measurement with the results of the second reference material measurement to obtain heat flux data for the second sample with respect to the second reference material,
 wherein steps (b)–(e) may be performed either before or after steps (f)–(i), step (j) may be performed at any point after step (e), and step (k) may be performed at any point after step (i).

28. The dual sample power compensated differential scanning calorimetry method of claim 27, wherein the substrate has a moderate thermal diffusivity, such that the sensor is characterized by having high calorimetric sensitivity.

29. The dual sample power compensated differential scanning calorimetry method of claim 27, further comprising:
 (l) calculating the heat flow to the sample materials;
 (m) calculating the heat flow to the reference materials;
 (n) plotting the difference between the heat flow to the sample materials and the heat flow to their respective reference materials as a function of the temperature of the samples;
 (o) identifying at least one transition in each plot so obtained;
 (p) determining the baseline for at least one of the transitions identified in step (o); and
 (q) determining the total heat of transition of the at least one transition.

30. The dual sample power compensated differential scanning calorimetry method of claim 27, wherein the substrate is a high thermal diffusivity material, such that the sensor is characterized by having a high resolution.

31. The dual power compensated differential scanning calorimetry method of claim 27, wherein the substrate is a high thermal diffusivity material, such that the sensor is characterized by having a high resolution.

32. The differential thermal analysis sensor of claim 1, further comprising (e) a second layer of insulating material attached to said substrate over said second thermopile;

(f) a third thermopile attached over said second layer of insulating material to said surface of said substrate, said third thermopile having a third set of measuring junctions positioned around a third measuring zone, and a third set of thermoelectric reference junctions, wherein said third set of thermoelectric reference junctions are attached to the second layer of insulating material, said third thermopile also being characterized by a low electrical impedance;

(g) a third layer of insulating material attached to said substrate over said third thermopile; and (h) a fourth thermopile attached over said third layer of insulating material to said major surface of said substrate, said fourth thermopile having a fourth set of measuring junctions positioned around a fourth measuring zone, and a fourth set of thermoelectric reference junctions, wherein said thermoelectric reference junctions are attached to the third layer of insulating material, said fourth thermopile also being characterized by a low electrical impedance;

wherein said first, second, third and fourth thermopiles have a common reference zone.

33. The differential thermal analysis sensor of claim 22, wherein the substrate is a high thermal diffusivity material, such that the sensor is characterized by having a high resolution.

34. The differential thermal analysis sensor of claim 32, wherein the first, second, third and fourth thermopiles are each comprised of in-series thermocouples, said thermocouples being comprised of thermoelements fabricated using thin film techniques.

35. The differential thermal analysis sensor of claim 32, wherein the first, second, third and fourth thermopiles are each comprised of in-series thermocouples, said thermocouples being comprised of thermoelements fabricated using thick film techniques.

36. The differential thermal analysis sensor of claim 32, wherein the first, second, third and fourth thermopiles are each comprised of in-series thermocouples having measuring junctions and thermoelectric reference junctions, the measuring junctions of said thermocouples of each said thermopile being arranged in a circular pattern to form each measuring zone.

37. The differential thermal sensor of claim 32, wherein the substrate has a low thermal diffusivity, such that the sensor is characterized by having very high calorimetric sensitivity.

38. The differential thermal analysis sensor of claim 32, wherein the substrate has a moderate thermal diffusivity, such that the sensor is characterized by having high calorimetric sensitivity.

39. The differential scanning calorimeter comprising:
(a) a temperature-controlled enclosure;
(b) a differential thermal sensor placed within the enclosure having a first low-impedance thermopile and a second low-impedance thermopile, wherein the first low-impedance thermopile comprises a first set of measuring junctions positioned around a first measuring position and the second low-impedance thermopile comprises a second set of measuring junctions positioned around a second measuring position, wherein each thermopile also comprises a set of thermoelectric reference junctions, and wherein the thermoelectric reference junctions of the first and second thermopiles are positioned in a common reference zone, said thermoelectric reference junctions being attached to the substrate such that the reference junctions of the first and second thermopiles are coincident;
(c) a first differential temperature amplifier and a second differential temperature amplifier, electrically connected to the differential thermal sensor such that the output of the first thermopile is fed to the first differential temperature amplifier and the output of the second thermopile is fed to the second differential temperature amplifier;
(d) analog to digital converters connected to each of the differential temperature amplifiers for converting the outputs of the temperature amplifiers into digital data; and
(e) means for combining and storing the digital data, and means for calculating the heat flow to and from the first position relative to the heat flow to and from the second position.

40. The differential scanning calorimeter of claim 39, further comprising means for providing thermal programs to control the temperature of the enclosure according to the thermal programs, and means for analyzing the heat flow data.

41. The differential scanning calorimeter of claim 39, further comprising a first thermocouple for measuring the temperature of the first position, a second thermocouple for measuring the temperature of the second position, and means for feeding the output of said first and second thermocouple to said means for combining and storing the digital data.

42. A power compensation differential scanning calorimeter comprising:
(a) a temperature-controlled enclosure;
(b) a differential thermal sensor placed within the enclosure having a first low-impedance thermopile and a second low-impedance thermopile, wherein the first low-impedance thermopile pumps heat to and from a temperature-controlling junction at a first position from and to a first heat source/sink junction and the second low-impedance thermopile pumps heat to and from a temperature-controlling junction at a second position from and to a second heat source/sink junction, the temperature-controlling junctions of each thermopile being positioned in its own separate temperature-controlling zone, and the heat source/sink junctions of the two thermopiles being attached to the substrate in a heat source/sink zone common to the two thermopiles, and wherein the heat source/sink junctions of the first and second thermopiles are coincident;
(c) a first thermocouple measuring the temperature of the first position and a second thermocouple measuring the temperature of the second position;
(d) means for controlling the current to the first and second thermopiles so as to suppress the difference in the temperatures measured by the first and second thermocouples;
(e) means for recording the currents supplied to the first and second thermocouples as a function of the temperature measured by the first thermocouple; and
(f) means for calculating the heat flow to and from the first position relative to the heat flow to and from the second position, as a function of the temperature measured by the first thermocouple, from the difference between the current supplied to the first thermopile and the current supplied to the second thermopile.

43. The power compensation differential scanning calorimeter of claim 43, further comprising means for switching the calorimeter from single-sample operation to dual sample operation.

* * * * *